United States Patent
Stein

(10) Patent No.: US 12,295,864 B2
(45) Date of Patent: *May 13, 2025

(54) EXPANDABLE FUSION IMPLANT AND RELATED METHODS

(71) Applicant: NuVasive, Inc., San Diego, CA (US)

(72) Inventor: Christopher Stein, Fallbrook, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,251

(22) Filed: Mar. 12, 2024

(65) Prior Publication Data

US 2024/0207066 A1 Jun. 27, 2024

Related U.S. Application Data

(63) Continuation of application No. 18/312,153, filed on May 4, 2023, now Pat. No. 11,957,602, which is a continuation of application No. 17/221,546, filed on Apr. 2, 2021, now Pat. No. 11,679,000, which is a continuation of application No. 16/265,050, filed on Feb. 1, 2019, now abandoned, which is a continuation of application No. 15/783,977, filed on Oct. 13, 2017, now Pat. No. 10,219,915, which is a continuation of application No. 14/285,590, filed on May 22, 2014, now Pat. No. 9,788,971.

(60) Provisional application No. 61/826,299, filed on May 22, 2013.

(51) Int. Cl.
 A61F 2/44 (2006.01)
 A61F 2/30 (2006.01)
 A61F 2/46 (2006.01)

(52) U.S. Cl.
 CPC .... *A61F 2/447* (2013.01); *A61F 2002/30265* (2013.01); *A61F 2002/30556* (2013.01); *A61F 2002/30579* (2013.01); *A61F 2002/30593* (2013.01); *A61F 2002/30622* (2013.01); *A61F 2002/30828* (2013.01); *A61F 2002/4627* (2013.01)

(58) Field of Classification Search
 CPC ...... A61F 2/4455; A61F 2/446; A61F 2/4465; A61F 2/447
 See application file for complete search history.

(56) References Cited

U.S. PATENT DOCUMENTS

2008/0147193 A1* 6/2008 Matthis ................. A61F 2/4465
 623/17.16
2013/0023994 A1* 1/2013 Glerum ................... A61F 2/447
 623/17.16

* cited by examiner

*Primary Examiner* — Si Ming Ku

(57) ABSTRACT

An expandable spinal fusion implant including first and second endplates coupled to an expansion member that sits within a housing. The expansion member is translated by a drive mechanism, whereby translation of the expansion member by the drive mechanism in a distal and proximal directions causes the distance between the endplates to increase and decrease, respectively.

19 Claims, 8 Drawing Sheets

EXPANDABLE FUSION IMPLANT AND RELATED METHODS

CROSS REFERENCE TO RELATED APPLICATIONS

This application is a continuation of U.S. patent application Ser. No. 18/312,153 filed on May 4, 2023, which is a continuation of U.S. patent application Ser. No. 17/221,546, filed Apr. 2, 2021, which is a continuation of U.S. patent application Ser. No. 16/265,050 filed on Feb. 1, 2019, which is a continuation of U.S. patent application Ser. No. 15/783,977 filed on Oct. 13, 2017, now U.S. Pat. No. 10,219,915, which is a continuation of U.S. patent application Ser. No. 14/285,590 filed on May 22, 2014, now U.S. Pat. No. 9,788,971, which claims priority to U.S. provisional application No. 61/826,299 filed on May 22, 2013, each of which is incorporated by reference in its entirely herein.

BACKGROUND

This application generally relates to an expandable spinal fusion implant for use in spinal surgery.

SUMMARY

To reduce risk of neural injury, the device will have the ability to be implanted to an intervertebral disc space in a collapsed state and expanded to a desired height. Expansion will be accomplished by translating an expansion mechanism mated to the inferior and superior endplates. In addition, a large aperture at the proximal end of the device allows for post packing of bone graft material into the hollow interior of the device, which is in communication with a fusion aperture in each of the superior and inferior endplates. In order to have the large through aperture at the proximal end of the device, the drive mechanism is offset from the width centerline of the device.

The device includes a housing, expansion mechanism, support rails, superior endplate, inferior endplate, endplate retainer, endplate safety retainer, drive mechanism, and drive mechanism retainer.

The expansion mechanism rides on rails that are retained partially in both the housing and expansion mechanism. There is one rail on each of the two lateral sides of the device. The expansion mechanism has ramps that are on the superior and inferior sides at both the distal and proximal ends. The ramps on the superior side mate with the superior endplate and the ramps on the inferior side mate with the inferior endplate. The expansion member includes a hollow interior for receiving bone graft material and for allowing bone growth therethrough. The hollow interior of the expansion mechanism is in communication with fusion apertures in each of the superior and inferior endplates.

To achieve expansion and contraction the endplates must be fixed in the longitudinal direction during translation of the expansion mechanism. An endplate retainer housed within the distal end of the housing mates with both the superior and inferior endplates and prohibits translation of the endplates, but allows for expansion.

The expansion mechanism is translated by advancing the drive mechanism, which is retained within the proximal end of the housing and offset from the width centerline. This offset allows for the large through cannula and post packing of bone graft material. The drive mechanism is mated to the expansion mechanism with the drive mechanism retainer. Advancement of the drive mechanism toward the distal end of the device allows the endplates to expand, while the withdrawal of the drive mechanism toward the proximal end of the device results in contraction of the endplates.

An endplate safety retainer located in the expansion mechanism prohibits the removal of the superior and inferior endplates from the expansion mechanism. Superior and inferior in flat and lordotic configurations are contemplated for use with the device described herein.

DETAILED DESCRIPTION

Figure 1:
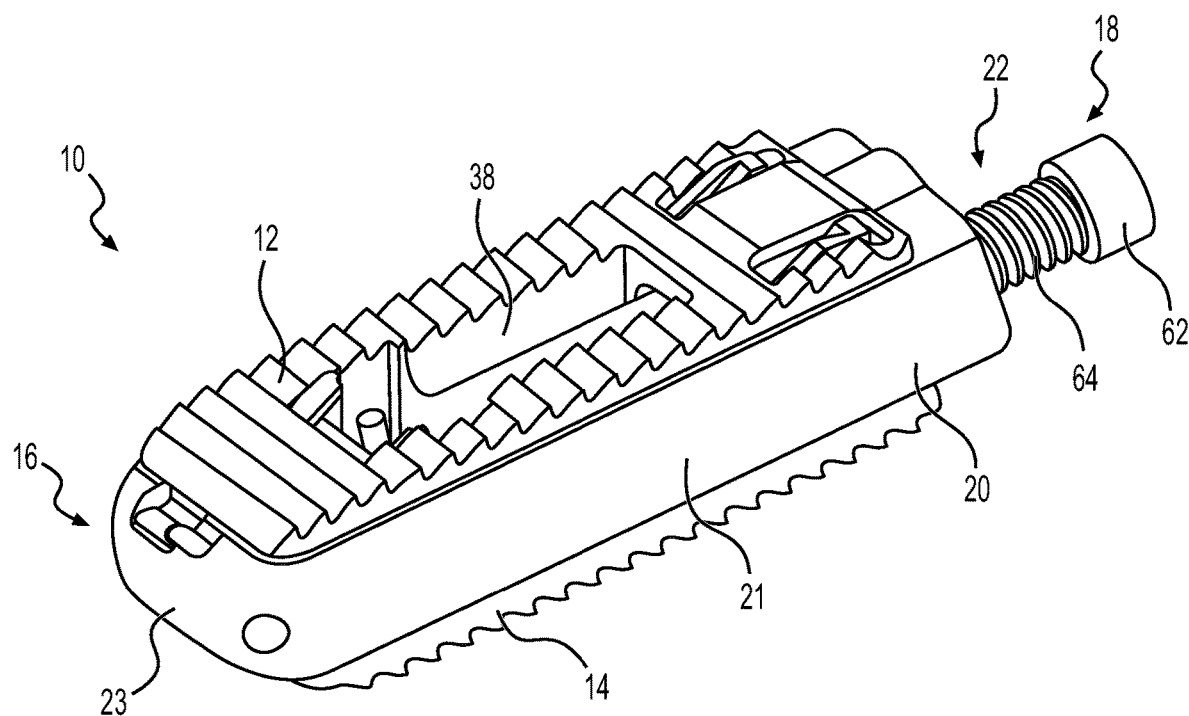
FIG. 1 is a perspective view of an exemplary embodiment of an expandable spinal fusion implant in its collapsed state.
Figure 2:
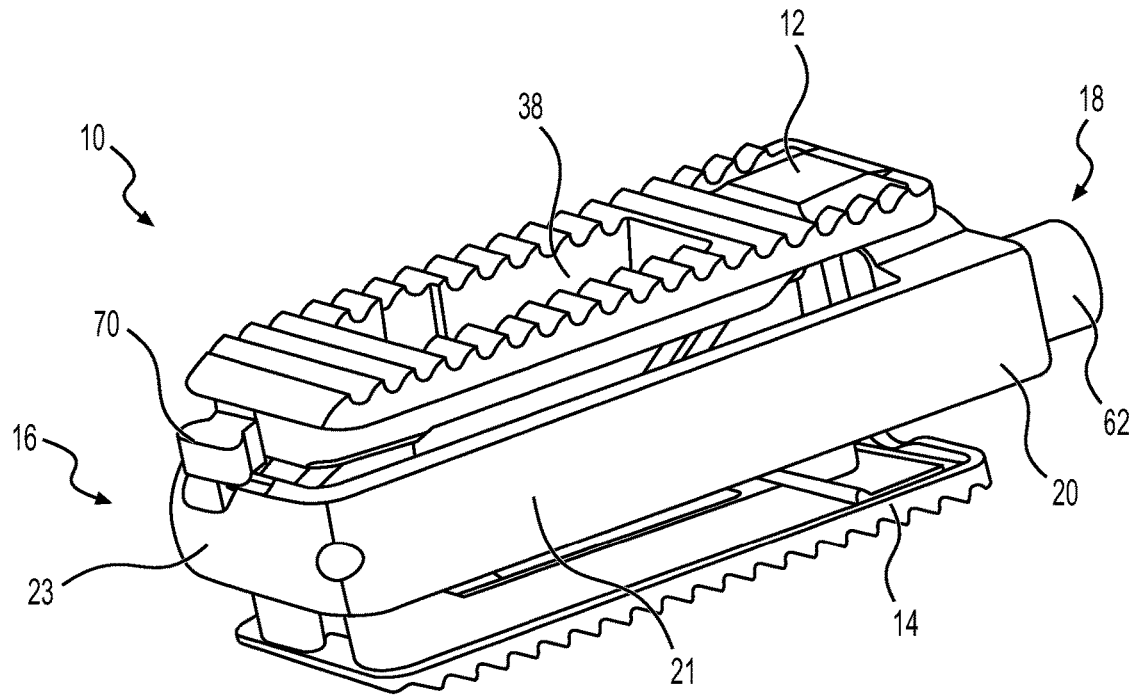
FIG. 2 is a perspective view of the expandable spinal fusion implant of FIG. 1 in its expanded state.
Figure 3:
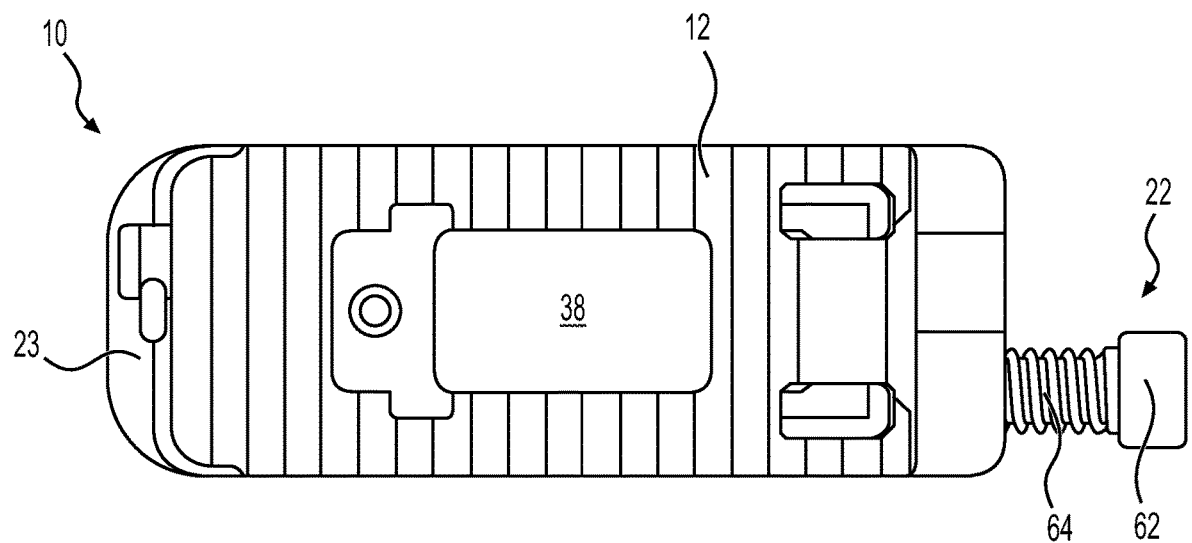
FIG. 3 is a top view of the expandable spinal fusion implant of FIG. 1.
Figure 4:
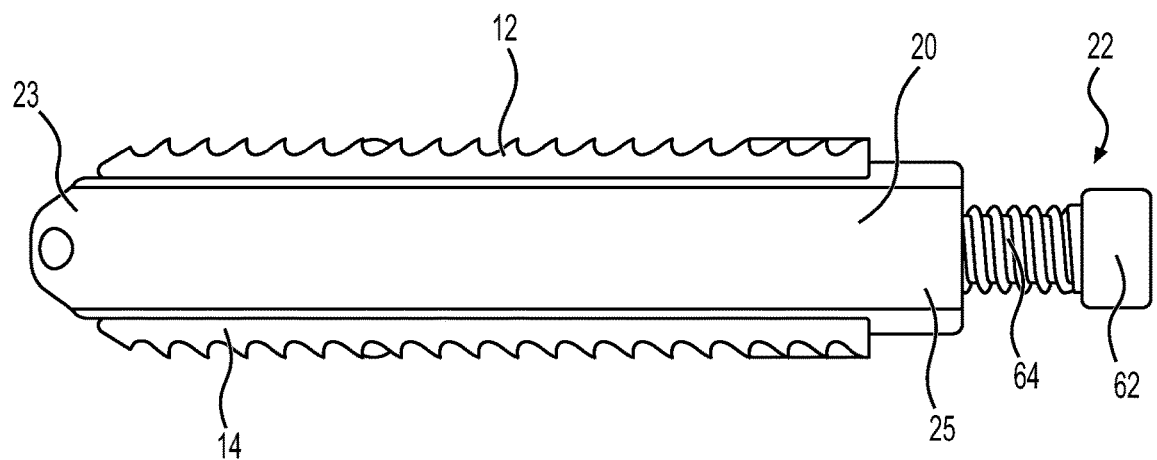
FIG. 4 is a side view of the expandable spinal fusion implant of FIG. 1 in its collapsed state.
Figure 5:
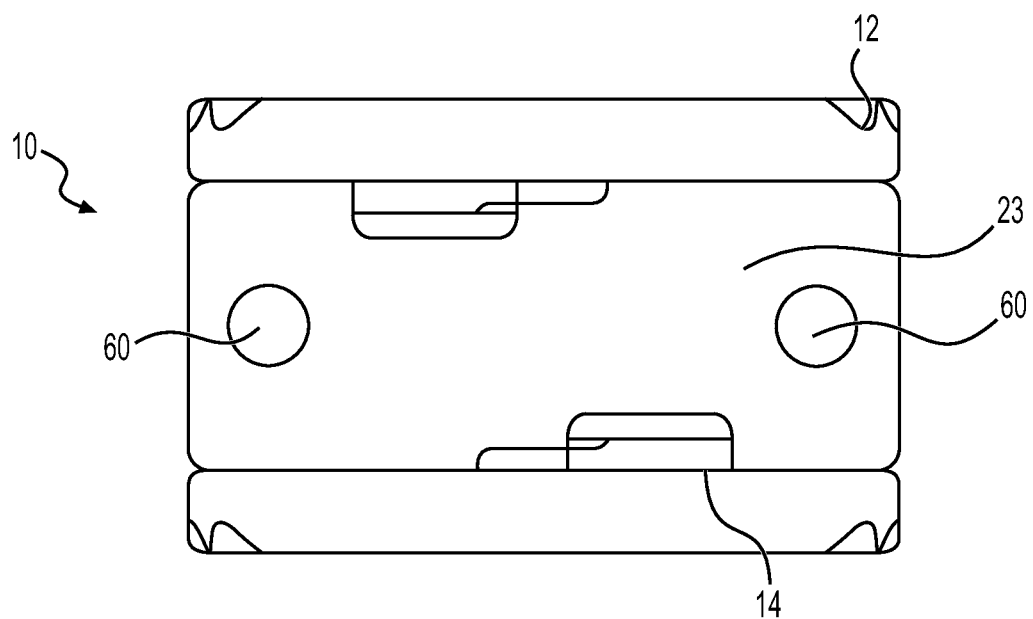
FIG. 5 is a leading end view of the expandable spinal fusion implant of FIG. 1 in its collapsed state.

FIGS. 1-13 illustrate an expandable spinal fusion implant for use during spinal surgery for implantation to an intervertebral disc space. According to an exemplary embodiment, the device is dimensioned for posterior approach surgery, e.g. posterior lumber interbody fusion (PLIF) and transforaminal lumbar interbody fusion (TLIF) approaches. However, according to an alternative embodiment, the device may also be dimensioned for use in a lateral approach to the anterior column of the spine. To reduce the risk of neural injury, the expandable spinal fusion implant has the ability to be implanted in a collapsed state (see FIG. 1) and expand to a height determined by the user (see FIG. 2). Expansion is accomplished by translating a wedge shaped expansion mechanism that is mated to the inferior and superior endplates 14, 12. As the expansion mechanism 26 is advanced towards the distal or leading end 16 of the implant 10 the endplates expand in height. To reduce the height of the implant or return the endplates back to their start position the expansion mechanism is advanced towards the proximal end of the device. In addition, a large cannula at the trailing or proximal end of the device allows for post packing of bone graft material, i.e. filling the interior of the device with bone graft after the device has been inserted into the intervertebral space and expanded to the desired height. The ability to post pack improves the chances of a successful surgical outcome by allowing for insertion of a sufficient amount of bone graft in adequate contact with the vertebral body endplates adjacent the disc space to promote bone growth.

As shown in FIGS. 1-13, the expandable spinal fusion implant 10 has a top endplate 12 and a bottom endplate 14. The endplates 12, 14 have substantially identical features as will be further described. Each endplate has a bone contacting surface 46 and an interior surface 48. As shown in the exemplary embodiment, the bone contacting surfaces 46 may have anti-migration features 44. The interior surfaces 48 of the endplates 12, 14 have ramped portions 36 that correspond to the angles of the ramps 34, 35 on the expansion mechanism 26. The ramped portions 36 of the interior endplates also include a male dovetail feature 40 that mates with the female dovetail feature 38 on the ramps 34 of the expansion mechanism 26. Each endplate 12, 14 has a central fusion aperture 38 to allow for bone growth through the implant 10 and with the endplates of the adjacent vertebral bodies. In order for each endplate 12, 14 to expand it must remain stationary in the longitudinal axis as the expansion mechanism 26 translates both proximally and distally. Both endplates 12, 14 further include a distal extension 70 to aid in retaining the endplates within the housing 20. While the implant 10 according to an exemplary embodiment in FIGS. 1-13 is shown with flat endplates, endplates having built in lordosis, i.e. having a distal height extending from the bone contacting surface to the interior surface that is greater than the proximal height, are also contemplated.

The expandable spinal fusion implant 10 includes an expansion mechanism 26 located between the top and bottom endplates 12, 14. The expansion mechanism 26 has two wedge portions 50, each of which has a superior ramp 34 and an inferior ramp 35 that correspond to and mate with the ramped portions 36, 37 of the superior and inferior endplates, respectively. Each endplate 12, 14 mates to the expansion mechanism 26 by an undercut or dovetail connection, at both the proximal end and the distal end, that allows movement between the wedge 50 and the endplate 12, 14. Each of the superior ramps 34 and inferior ramps 35 include a female dovetail feature 38 that mates with the male dovetail features 36 on the endplates 12, 14. An endplate safety retainer is housed within the expansion mechanism to prohibit removal of the endplates once assembled. The expansion mechanism 26 has a recess 56 at its proximal end dimensioned to receive the drive mechanism retainer 24 therein. The expansion mechanism 26 has a hollow interior defining a central fusion aperture 39 that aligns with the central fusion aperture 38 of the top and bottom endplates 12, 14 to allow for bone growth therethrough. The distal wedge 50 of the expansion mechanism 26 includes an endplate safety retainer 32 extending therethrough to prevent the dislocation of the endplates 12, 14 from the expansion mechanism 26.

Figure 6:
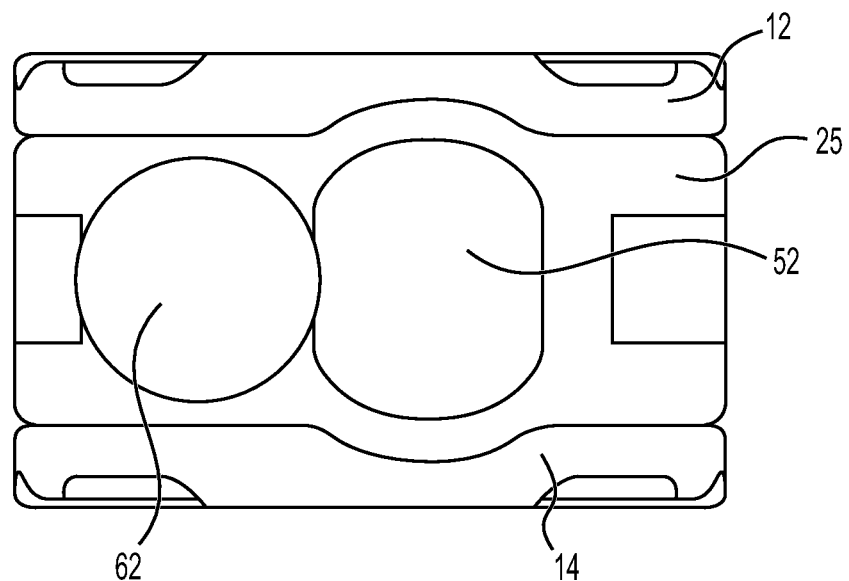
FIG. 6 is a trailing end view of the expandable spinal fusion implant of FIG. 1 in its collapsed state.
Figure 7:
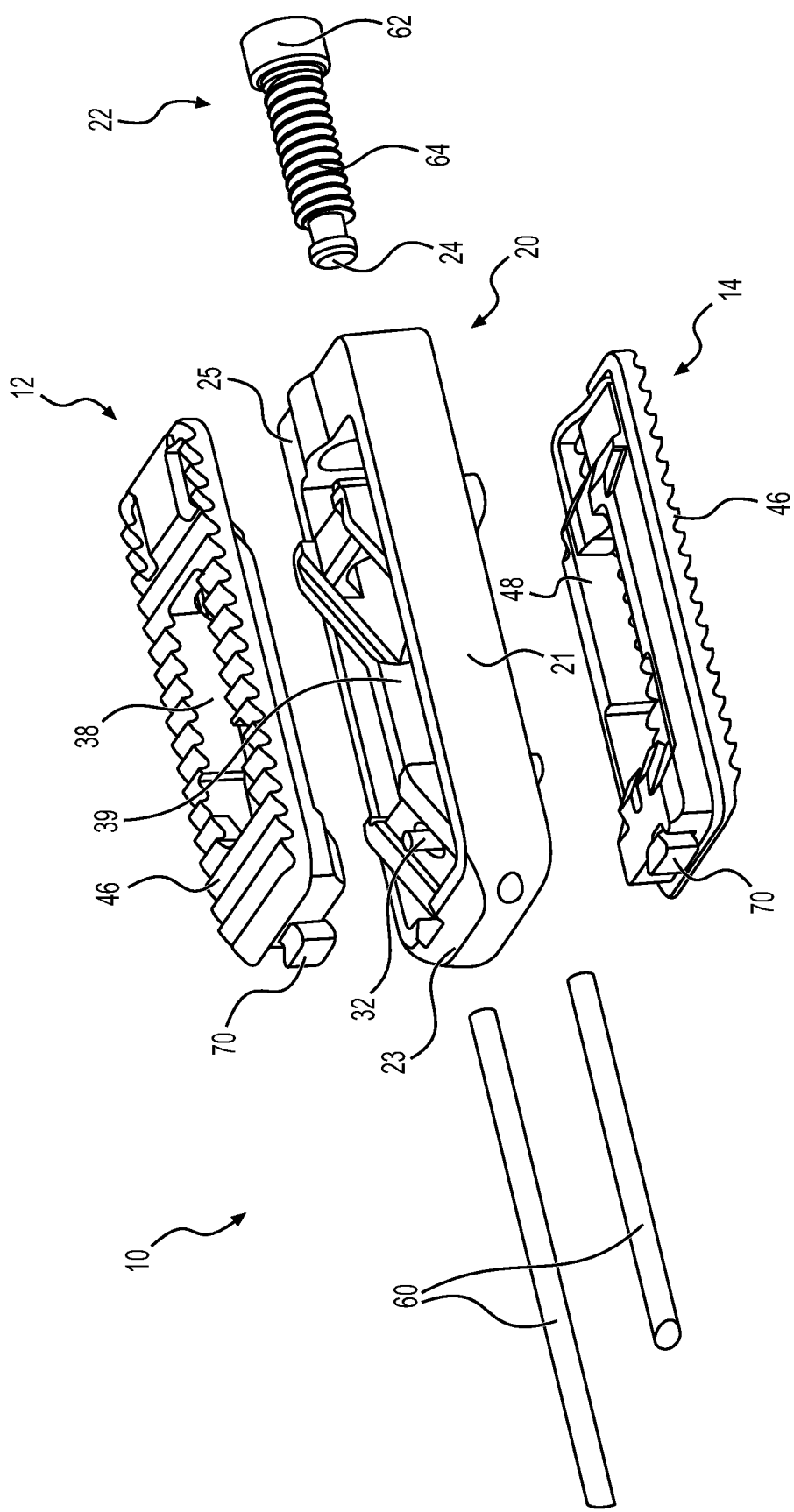
FIG. 7 is an exploded view of the expandable spinal fusion implant.
Figure 8:
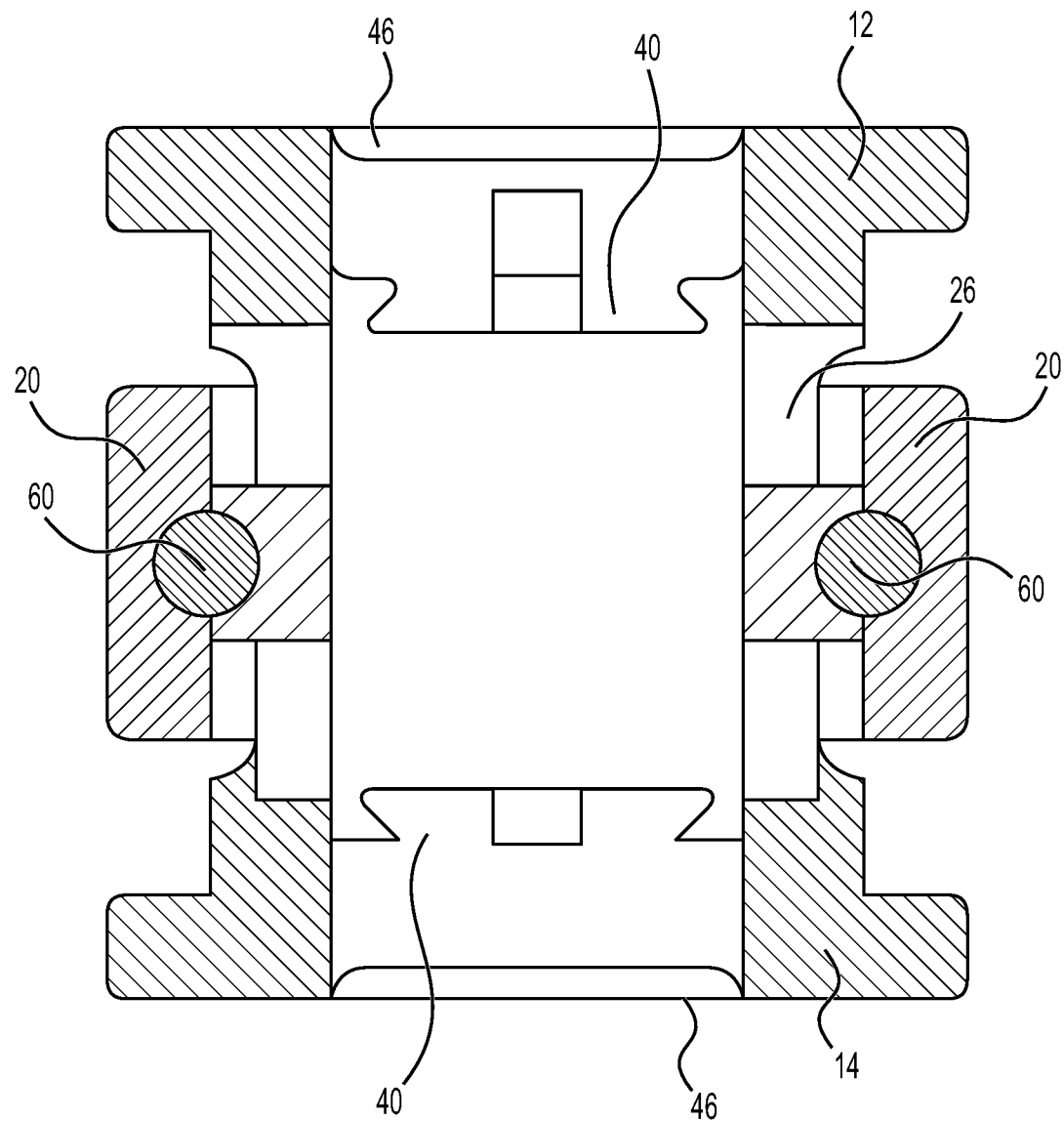
FIG. 8 is a cross sectional view of the leading end of expandable spinal fusion implant in its expanded state.
Figure 9:
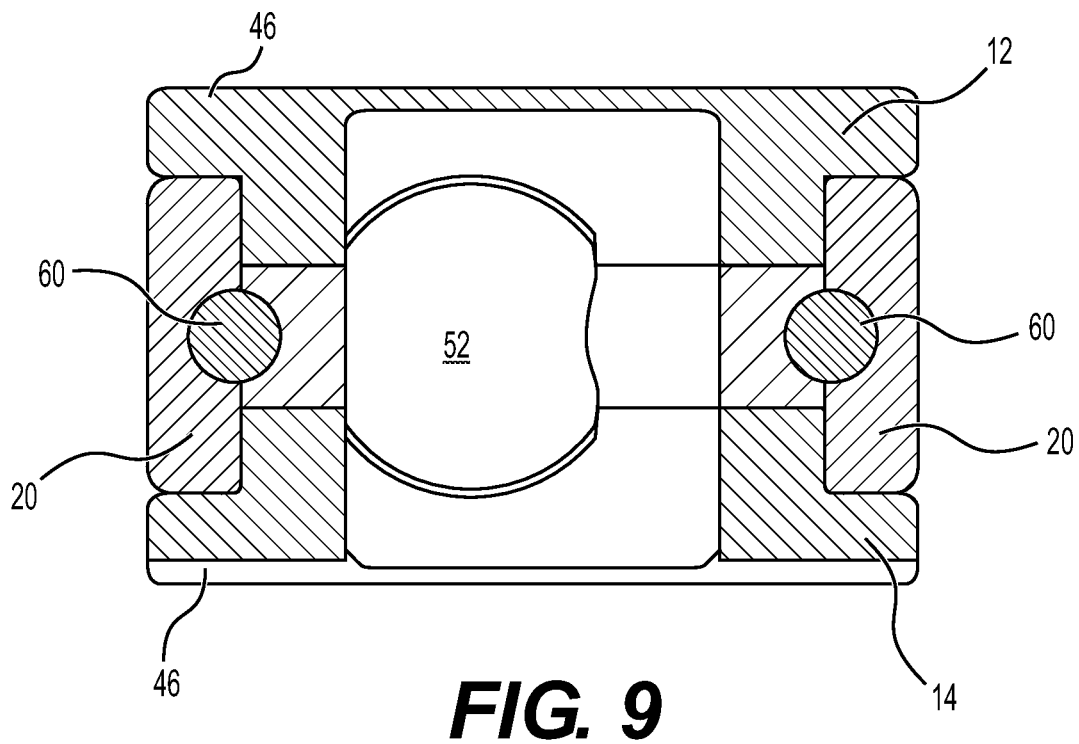
FIG. 9 is a cross sectional view of the trailing end of the expandable spinal fusion implant in its collapsed state.
Figure 10:
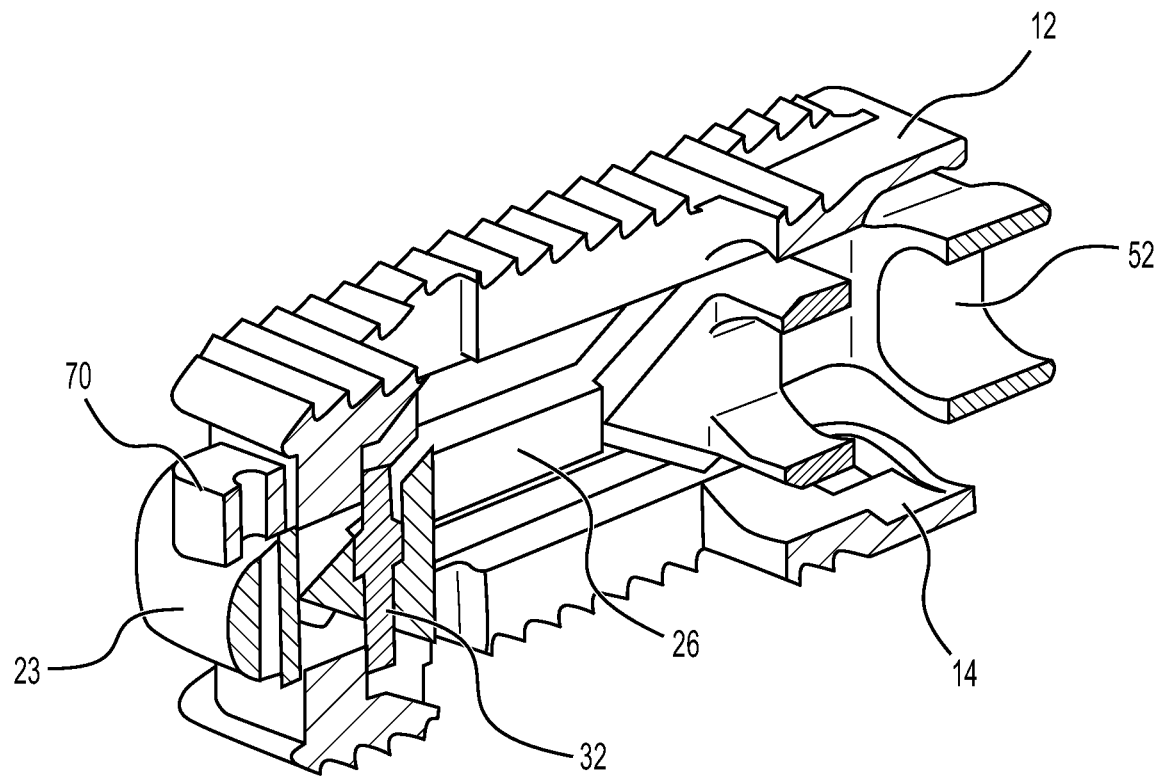
FIG. 10 is a cross sectional view of the expandable spinal fusion implant.
Figure 11:
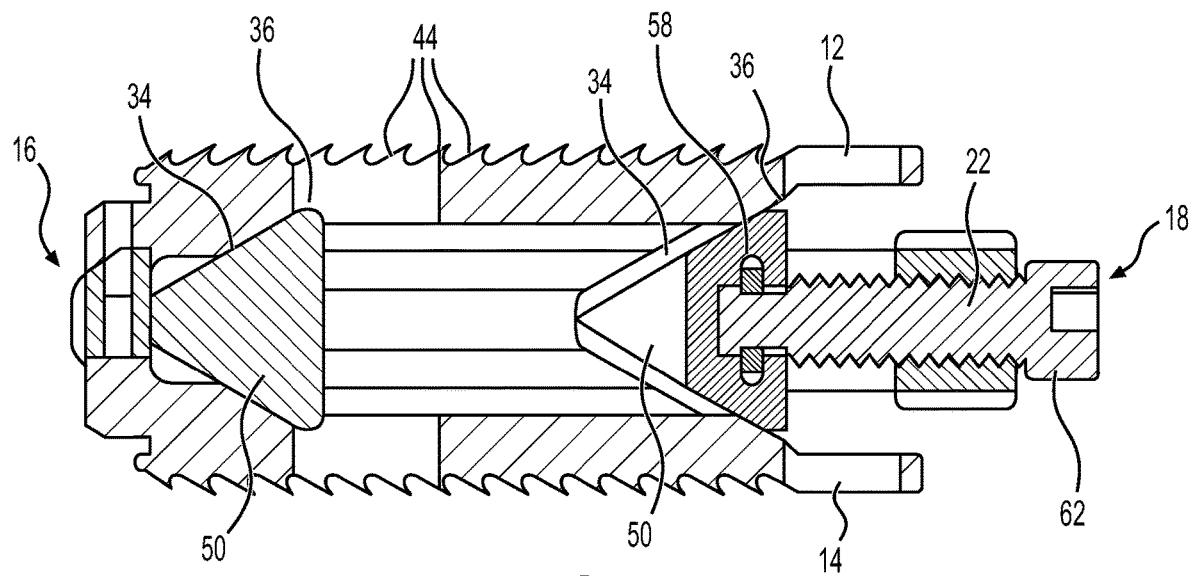
FIG. 11 is a cross sectional view of the expandable spinal fusion implant.
Figure 12:
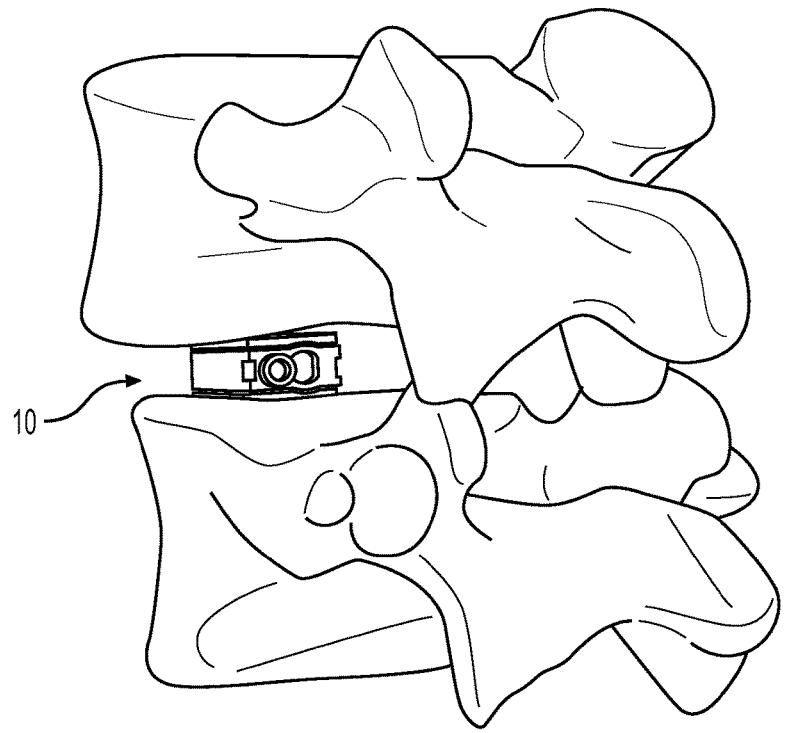
FIG. 12 is a perspective view of the expandable spinal fusion implant after insertion into the disc space.
Figure 13:
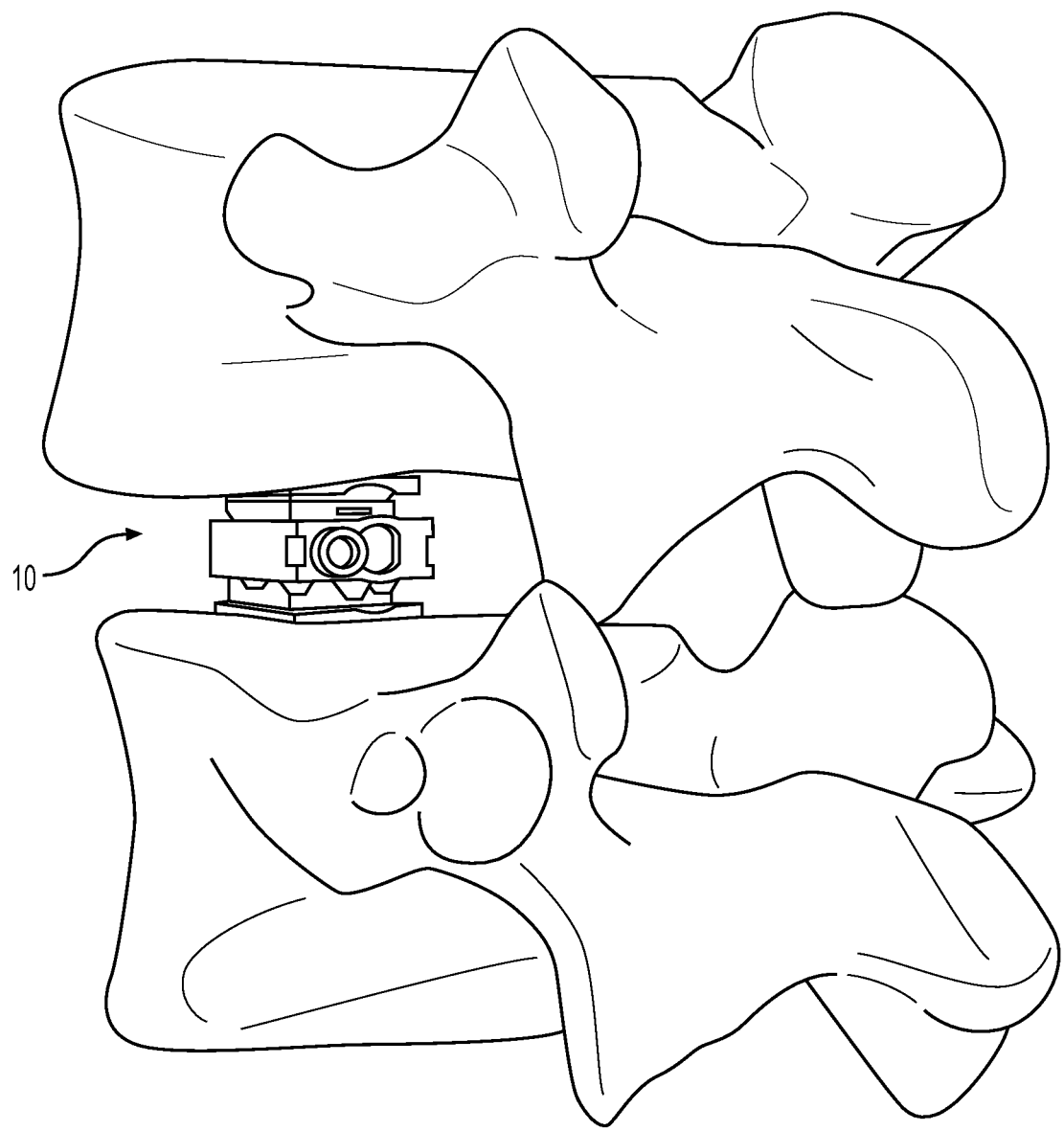
FIG. 13 is a perspective view of the expandable spinal fusion implant in its fully expanded state in the disc space.

As best shown in FIG. 7, the expandable spinal fusion implant 10 also includes a housing 20 dimensioned to house the expansion mechanism 26. The expansion mechanism 26 is supported in the housing 20 by two support rails 60. The housing 20 is defined by opposing lateral walls 21, a distal wall 23 and a proximal wall 25. The housing 20 has a longitudinal length that exceeds the longitudinal length of the endplates 12, 14. The distal wall 23 of the housing is tapered to aid in insertion of the implant 10. The distal wall 23 also includes recesses 58 for receiving the distal extensions 50 of the endplates 12, 14 to retain the endplates within the housing 20. As seen in FIG. 6, the proximal wall 25 of the housing 20 includes a cannula 52 for receiving bone graft material into the central fusion aperture 39 of the expansion mechanism 26 as well as a threaded drive mechanism aperture 54 for receiving the drive mechanism 22 therethrough.

According to the exemplary embodiment, the drive mechanism 22 has a head 62 at its proximal end for engaging an actuator tool (not shown) and a threaded shaft 64 extending from the head 62 and terminating at the distal end with a drive mechanism retainer 24 configured to anchor the drive mechanism 22 to the expansion mechanism 26. The purpose of the drive mechanism 22 is to translate the expansion mechanism 26 both proximally and distally. The threaded shaft 64 of the drive mechanism 22 engages with the threaded aperture 54 of the housing 20 at the proximal end 25 and also mates with the recess 56 at the proximal end of the expansion mechanism 26 and is retained with the expansion mechanism 26 by a drive mechanism retainer 24. As best seen in FIG. 6, the drive mechanism 22 is located at a position within the implant 10 that is offset from the central longitudinal axis of the implant 10 to allow for post packing of bone graft through the cannula 52 and into the central fusion aperture 39.

According to the exemplary embodiment, the expandable spinal fusion implant 10 is implanted into a patient by first accessing the desired intervertebral disc space via lateral approach to the anterior spinal column or a posterior (e.g. PLIF or TLIF) approach. The implant 10 is inserted in its collapsed state into the intervertebral disc space and maneuvered into a desired position. Once the desired position is reached, a tool is engaged with the drive mechanism 22 to turn the drive mechanism 22 and thereby urge the expansion mechanism 26 in the distal direction and consequently increase the distance between the top and bottom endplates 12, 14. The drive mechanism 22 can then be turned in the opposite direction to urge the expansion mechanism 26 in the proximal direction in order to decrease the distance between the endplates 12, 14 if necessary. Once the implant 10 has been set at the desired height, bone graft can be introduced through the cannula 52 in the proximal end 25 of the housing 20 to the interior of the implant 10, into the central fusion apertures 38, 39 of the expansion mechanism 26 and endplates 12, 14.

What is claimed is:

1. An expandable implant comprising:
a housing having a central longitudinal axis,
first and second endplates,
an expansion mechanism positioned within the housing, and
a drive mechanism;
wherein the drive mechanism is inserted through a drive mechanism aperture in a proximal wall of the housing;
wherein the drive mechanism is rotated and translated along a longitudinal axis that is offset from the central longitudinal axis of the housing;
wherein a distal end of the drive mechanism or a portion thereof is configured to be received within a recess in the expansion mechanism; and
wherein the expansion mechanism is translated relative to the housing, thereby changing a distance between the first and second endplates.

2. The expandable implant of claim 1, further comprising:
in a collapsed state of the expandable implant, positioning the expandable implant in an intervertebral disc space of a subject; and
translating the expansion mechanism distally to increase the distance between the first and second endplates in an expanded state of the expandable implant.

3. The expandable implant of claim 1, wherein the drive mechanism comprises a head at a proximal end, a shaft extending from the head and terminating at a distal end of the drive mechanism, and a drive mechanism retainer at the distal end.

4. The expandable implant of claim 3, wherein inserting the drive mechanism further comprises threadedly engaging the shaft of the drive mechanism with the drive mechanism aperture.

5. The expandable implant of claim 1, wherein the expansion mechanism comprises a drive mechanism retainer at a proximal end thereof, and the drive mechanism retainer retains at least a portion of the drive mechanism within the expansion mechanism.

6. The expandable implant of claim 1, wherein the central longitudinal axis of the housing extends between the proximal wall and a distal wall of the housing.

7. The expandable implant of claim 1, wherein the longitudinal axis is offset from and parallel to the central longitudinal axis of the housing.

8. The expandable implant of claim 1, further comprising rotating the drive mechanism in a first direction about the longitudinal axis, thereby translating the expansion mechanism toward a distal wall of the housing, wherein the translating causes the distance between the first and second endplates to increase.

9. The expandable implant of claim 8, further comprising rotating the drive mechanism about the longitudinal axis in a second direction opposite the first direction, thereby translating the expansion mechanism away from the distal wall of the housing, wherein the translating causes the distance between the first and second endplates to decrease.

10. The expandable implant of claim 1, further comprising translating the expansion mechanism on a plurality of rails disposed at least partially within the housing.

11. The expandable implant of claim 1, wherein each of the first and second endplates includes an interior surface having a ramped portion, and the expansion mechanism comprises a first wedge and a second wedge positioned at a proximal end and a distal end thereof, respectively, wherein translating the expansion mechanism toward the distal wall of the housing comprises engaging each of the first and second wedges with a corresponding ramped portion of the first and second endplates.

12. The expandable implant of claim 11, wherein each of the first and second wedges includes a ramp having a sloped surface that at least partially faces toward the distal wall of the housing.

13. The expandable implant of claim 1, further comprising limiting movement of the first and second endplates along the central longitudinal axis of the housing while translating the expansion mechanism.

14. The expandable implant of claim 13, wherein limiting the movement of the first and second endplates further comprises receiving a distal extension of each of the first and second endplates in a corresponding recess in a distal wall of the housing and retaining the first and second endplates within the housing.

15. The expandable implant of claim 1, wherein the expansion mechanism comprises an endplate safety retainer at a distal end thereof, and the the endplate safety retainer couples each of the first and second endplates to the expansion mechanism.

16. The expandable implant of claim 1, wherein each of the first and second endplates includes an endplate fusion aperture extending therethrough and in communication with the hollow interior of the expansion mechanism.

17. The expandable implant of claim 1, wherein the proximal wall of the housing has an injection aperture for receiving a bone graft material.

18. The expandable implant of claim 17, wherein the injection aperture extends along the central longitudinal axis of the housing and is offset from the drive mechanism aperture.

19. The expandable implant of claim 1, wherein the length of a proximal end of the first endplate is longer than the length of a distal end of the first endplate, and wherein the length of a proximal end of the second endplate is longer than the length of a distal end of the second endplate.

* * * * *